(12) United States Patent
Beitle et al.

(10) Patent No.: US 10,442,842 B2
(45) Date of Patent: Oct. 15, 2019

(54) CLEAVAGE RESISTANT PHOTOLUMINESCENT PROTEINS AND APPLICATIONS THEREOF

(71) Applicant: THE BOARD OF TRUSTEES OF THE UNIVERSITY OF ARKANSAS, Little Rock, AR (US)

(72) Inventors: Robert R. Beitle, Fayetteville, AR (US); Rudra Palash Mukherjee, Fayetteville, AR (US); Suresh K. Thallapuranam, Fayetteville, AR (US); Joshua Sakon, Fayetteville, AR (US); David S. McNabb, Fayetteville, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 169 days.

(21) Appl. No.: 15/448,282

(22) Filed: Mar. 2, 2017

(65) Prior Publication Data
US 2017/0253640 A1    Sep. 7, 2017

Related U.S. Application Data

(60) Provisional application No. 62/302,447, filed on Mar. 2, 2016.

(51) Int. Cl.
*C07K 14/435*    (2006.01)
*B01D 15/08*    (2006.01)

(52) U.S. Cl.
CPC ........ *C07K 14/43595* (2013.01); *B01D 15/08* (2013.01)

(58) Field of Classification Search
CPC ........... G01N 33/5008; G01N 33/5014; G01N 33/533; C07K 1/1077
See application file for complete search history.

(56) References Cited

PUBLICATIONS

Nagasundarapandian Soundrarajan et al (Conjugation of Proteins by Installing BIO-Orthogonally Reactive Groups at Their N-Termini. PLoS One 2012; 7(10): pp. 1-9, Epub Oct. 8, 2012). (Year: 2012).*
Crameri et al (Improved Green Fluorescent Protein by Molecular Evolution Using DNA Shuffling. Nature vol. 14, 1996 (Year: 1996).*

* cited by examiner

*Primary Examiner* — Kagnew H Gebreyesus
(74) *Attorney, Agent, or Firm* — J. Clinton Wimbish; Nexsen Pruet, PLLC (57) ABSTRACT

Photoluminescent proteins resistant to protein cleavage reagents are described herein. In being resistant to cleavage reagents, such photoluminesncent proteins can reduce the number of digestion or cleavage products, thereby simplifying quantification and purification of recombinant protein compositions. In some embodiments, a photoluminescent protein described herein comprises an amino acid sequence having an absence of internal methionine residues.

19 Claims, 5 Drawing Sheets
Specification includes a Sequence Listing.

Figure 1. Trajectory of fed-batch fermentation for cells harboring $GFP_{UV}$ and $rGFP_{UV}$ Plasmids Figure 2A. Ion exchange chromatography of GFP$_{UV}$.

Figure 2B. Ion exchange chromatography of rGFP$_{UV}$.

Figure 3. SDS PAGE gels showing clarified lysate and enriched fraction of rGFPuv Figure 4. Trajectories of fluorescence of GFP$_{UV}$ and rGFP$_{UV}$ during digestion with cyanogen bromide.

CLEAVAGE RESISTANT PHOTOLUMINESCENT PROTEINS AND APPLICATIONS THEREOF

RELATED APPLICATION DATA

The present application claims priority pursuant to 35 U.S.C. § 119(e) to U.S. Provisional Patent Application Ser. No. 62/302,447 filed Mar. 2, 2016 which is incorporated herein by reference in its entirety.

FIELD

The present invention relates to photoluminescent proteins that are resistant to cleavage reagents and, in particular, to green fluorescent proteins exhibiting resistance to cleavage by cyanogen bromide (CNBr).

BACKGROUND

Overexpression and purification of recombinant proteins are of significant interest to the pharmaceutical and biochemical industries. Recombinant proteins, for example, are used in a variety of commercially important applications, including therapeutics, bioinsecticides, diagnostic kits and many others. Advances in recombinant deoxyribonucleic acid (DNA) technology and protein expression systems have rendered practical the production of proteins in significant quantities employing a variety of hosts. However, rapid and efficient purification and quantification of recombinant proteins remains a major challenge. In several instances, fluorescent proteins can be expressed with recombinant proteins for identification and quantification procedures. However, removal of the fluorescent protein markers can complicate recombinant protein purification. Such markers, for example, can be digested into multiple products resulting in complex mixtures that render recombinant protein isolation difficult.

SUMMARY

In view of the foregoing disadvantages, photoluminescent proteins resistant to protein cleavage reagents are described herein. In being resistant to cleavage reagents, such photoluminesncent proteins can reduce the number of digestion or cleavage products, thereby simplifying quantification and purification of recombinant protein compositions. In some embodiments, a photoluminescent protein described herein comprises an amino acid sequence having an absence of internal methionine residues. For example, the photoluminescent protein can be a modified green fluorescent protein comprising an amino acid sequence wherein internal methionine residues are substituted by one or more amino acid residues inert to cyanogen bromide (CNBr). In some embodiments, the amino acid sequence of the green fluorescent protein includes the sequence of SEQ ID NO:1. In being resistant to CNBr cleavage, the modified green fluorescent protein can reduce the number of digestion products in recombinant protein purification.

In another aspect, recombinant protein compositions are described herein. A recombinant protein composition comprises a first amino acid sequence of a target protein and a photoluminescent protein coupled to the first amino acid sequence, the photoluminescent protein comprising an amino acid sequence having an absence of internal methionine residues. In some embodiments, the photoluminescent protein is a modified green fluorescent protein. The modified green fluorescent protein can have an amino acid sequence including SEQ ID NO:1.

In a further aspect, methods of purifying recombinant protein compositions are described herein. A method of purifying a recombinant protein composition comprises providing a mixture including the recombinant protein composition, the recombinant protein composition comprising a first amino acid sequence of a target protein and a photoluminescent protein coupled to the first amino acid sequence, the photoluminescent protein including an amino acid sequence having an absence of internal methionine residues. The recombinant protein composition is subsequently treated with CNBr, releasing the recombinant protein from an intact photoluminescent protein. In some embodiments, the photoluminescent protein is a modified green fluorescent protein. The modified green fluorescent protein can have an amino acid sequence of SEQ ID NO:1.

These and other embodiments are described further in the following detailed description.

DETAILED DESCRIPTION

Embodiments described herein can be understood more readily by reference to the following detailed description and examples and their previous and following descriptions. Elements, apparatus and methods described herein, however, are not limited to the specific embodiments presented in the detailed description and examples. It should be recognized that these embodiments are merely illustrative of the principles of the present invention. Numerous modifications and adaptations will be readily apparent to those of skill in the art without departing from the spirit and scope of the invention.

I. Photoluminescent Proteins

Photoluminescent proteins having resistance to protein cleavage reagents are described herein. In being resistant to cleavage reagents, such photoluminesncent proteins can reduce the number of digestion or cleavage products, thereby simplifying quantification and purification of recombinant protein compositions. In some embodiments, a photoluminescent protein described herein comprises an amino acid sequence having an absence of internal methionine residues. For example, the photoluminescent protein can have no internal methionine residues. In some embodiments, the photoluminescent protein can be a modified green fluorescent protein comprising an amino acid sequence wherein all internal methionine residues are substituted by one or more amino acid residues inert or resistant to cyanogen bromide (CNBr). Any amino acid residue can be used as a methionine substitute under the condition the substitute residue does not preclude emission from the chromophore. Moreover, substitute residues can be the same throughout the amino acid sequence or the substitute residues may vary along the amino acid sequence. For example, different substitute amino acids can be employed depending on the environment of the methionine to be substituted. Suitable substitute amino acid residues can be selected according to several considerations including, but not limited to, the steric environment of the methionine, hydrophobic/hydrophilic character of the methionine environment and secondary, tertiary and/or quaternary structural considerations associated with the methionine environment. In some embodiments, a suitable substitute residue is leucine. In some embodiments, the amino acid sequence of the green fluorescent protein includes the sequence of SEQ ID NO:1.

Alternatively, an absence of internal methionine residues does not mean a complete absence of methionine residues in the photoluminescent protein. Methionine residues having positioning in the protein structure inaccessible to CNBr may not require substitution according to some embodiments herein. Further, variants of green fluorescent protein are also contemplated. Internal methionine residues of blue fluorescent protein (FP or BFP), cyan fluorescent protein (CFP), yellow fluorescent protein (YFP) and/or red fluorescent (RFP) can be substituted with one or more amino acid residues inert or resistant to CNBr.

II. Recombinant Protein Compositions

In another aspect, recombinant protein compositions are described herein. A recombinant protein composition comprises a first amino acid sequence of a target protein and a photoluminescent protein coupled to the first amino acid sequence, the photoluminescent protein comprising an amino acid sequence having an absence of internal methionine residues. The photoluminescent protein can have any structure recited in Section I above, including the modified green fluorescent protein and colored variants thereof. For example, in some embodiments, the green fluorescent protein includes the sequence of SEQ ID NO:1.

Various vectors encoding the target protein, associated photoluminescent protein can be employed. For example, plasmids or viral vectors can be used. Alternatively, yeast or mammalian vectors can be used. Appropriate amplification techniques and restriction enzymes are used to construct vectors for expression of the target protein and associated photoluminescent protein by a host. Moreover, the vector can include control sequences such as promoter sequences. Expression control sequences of the vector can vary depending on whether the vector is designed to express a nucleotide sequence in a prokaryotic or eukaryotic host. Expression control sequences may include transcriptional regulatory elements such as promoters, enhancer elements and transcriptional termination sequences, and/or translational regulatory elements, such as translational initiation and termination sites.

Once the vector encoding the target protein and photoluminescent protein is prepared, the vector is introduced into an appropriate host cell by any of a variety of suitable techniques, including transformation as known in the art. In some embodiments, for example, the constructed vector is inserted into bacterial host(s) such as Escherichia coli. After transformation, recipient cells are grown in an appropriate medium and overexpression of the target protein is administered.

III. Methods of Purifying Recombinant Protein Compositions

In a further aspect, methods of purifying recombinant protein compositions are described herein. A method of purifying a recombinant protein composition comprises providing a mixture including the recombinant protein composition, the recombinant protein composition comprising a first amino acid sequence of a target protein and a photoluminescent protein coupled to the first amino acid sequence, the photoluminescent protein including an amino acid sequence having an absence of internal methionine residues. The recombinant protein composition is subsequently treated with CNBr, releasing the recombinant protein from an intact photoluminescent protein. As described herein, the absence of methionine residues inhibits or precludes digestion of the photoluminescent protein into multiple products, thereby facilitating further purification by chromatography and/or other separation techniques. The photoluminescent protein can have any structure recited in Section I above, including the modified green fluorescent protein and colored variants thereof. For example, in some embodiments, the green fluorescent protein includes the sequence of SEQ ID NO:1. In some embodiments, the mixture comprising the recombinant protein composition is a lysate, such as that from the expressing host.

These and other embodiments are further illustrated in the following non-limiting example.

Example 1—Cleavage Resistant $GFP_{UV}$ ($rGFP_{UV}$)

Construction of rGFP Plasmid Harboring E.coli

A synthetic gene for expressing the protein of SEQ ID NO:1 was procured from Integrated DNA Technologies (Coralville, Iowa). Plasmid pBAD myc His A was obtained from Invitrogen (Carlsbad, Calif.). Restriction enzymes were obtained from New England Biolabs (Ipswich, Mass.). The synthetic gene and pBAD vector were double digested with NcoI and ECoRI enzymes. They were then purified and recovered using a two tier 1.2% agarose Recovery FlashGel cassette and FlashGel Recovery Buffer, obtained from Lonza (Rockland, Me.). The purified and digested pBAD vector and synthetic $rGFP_{UV}$ gene were then ligated overnight using T4 DNA ligase at 14° C. The ligation mixture was then used for transformation of chemically competent E. coli BL21 (DE3) obtained from Invitrogen (Grand Island, N.Y.) as per manufacturer instruction. To 50 µl of BL21 (DE3) competent cells, 200 ng of ligation mix was added and the mixture was placed on ice for 30 minutes. Cells were then heat shocked at 42° C. for 30 seconds; followed by addition of Super Optimal Broth with Catabolite repression (SOC) media and incubated at 37° C. for 60 minutes with vigorous shaking. Transformants were plated on plates containing 100 µg/ml ampicillin and 2 mg/ml arabinose. Colonies which had green fluorescence under UV illumination were selected, grown overnight at 37° C. and plated again. Using the same procedure, $pGFP_{UV}$ procured from Clonetech (Mountain View, Calif.), was transformed into chemically competent BL21 (DE3) cells and plated on agar plates containing 100 µg/ml ampicillin.

Expression of Proteins by High Cell Density Fed-Batch Fermentation

In a 50 ml falcon tube containing 5 ml of luria bertani (LB) media and 100 µg/ml ampicillin, a single colony of the transformed E. coli BL21 DE3; harboring $rGFP_{UV}$ plasmid, was transferred and incubated overnight at 37° C. in a shaker at 250 rpm. One ml of this seed culture was used to inoculate 100 ml LB medium containing appropriate amount of ampicillin in a 500 ml shaker flask and grown at 37° C. for 8 hours with shaking at 250 rpm. A 5 liter Applikon bioreactor (Foster City, Calif.) equipped with BioXpert Advisory software containing 3 liters of LB media and appropriate amount of ampicillin was inoculated with 50 ml of the previously grown culture. Using a heating jacket and cooling loop, the temperature of the bioreactor was maintained at 37° C. Using 7 M NH4OH, the pH of the fermentation broth was maintained at 6.8 while an external supply of pure oxygen was used to maintain the dissolved oxygen of the broth in bioreactor above 50% at all times. For real time monitoring of the optical density of the media, a Bugeye optical density probe (Buglab, Foster City, Calif.) was used. For feed, a 500 g/L sterilized glucose solution was used. The feed was started when the carbon present in the substrate initially was consumed, which occurred about 5 hours after start of fermentation. An exponential feeding profile was used by programming using the Applikon Bioexpert software. Arabinose was added to the bioreactor after 9 h of fermentation. Cell pellets were harvested by centrifugation at 5,000×g for 1 hour, 3° C. and were stored at −80° C. $GFP_{UV}$ was expressed using the same procedure by using the same procedure with the only difference IPTG being used as the inducer instead of arabinose.

Enrichment of $rGFP_{UV}$ and $GFP_{UV}$ and Analysis

For further purification steps, 5 g of cell pellets were resuspended in 15 ml of IEX DEAE Buffer A (25 mM Tris-HCl, pH=8). The cells were lysed using Q125 Sonicator at 40% amplitude using a procedure of a 10 second pulse and 15 second rest period for a total of 10 minutes. The lysed solution was then centrifuged at 5000×g at 3° C. A FPLC system from AKTA Amersham Pharmacia Biotech (Sweden) was used along with a 1 ml HiTrap DEAE FF column from GE Healthcare (Piscataway, N.J.). The column was first equilibrated with IEX DEAE Buffer A and the clarified lysate was loaded at 0.32 cm/min. The column was washed with 15 column volumes of IEX DEAE Buffer A at a flow rate of 0.64 cm/min. This was followed by a stepwise elution using IEX DEAE Buffer B (25 mM Tris-HCl, 1 M NaCl, pH=8). Fractions, 3 ml in volume, were collected and stored at −80° C. for further analysis. $GFP_{UV}$ fractions were enriched using the same procedure as $rGFP_{UV}$. The total protein content of clarified samples and enriched fractions was determined using a DC Protein Assay from Bio-Rad (Hercules, Calif.) according to instructions from manufacturer. A densitometric analysis was performed using ImageJ software.

Fluorometric Analysis of Cyanogen Bromide Cleavage

Using a RF-Mini 150 Recording Fluorometer manufactured by Shimadzy (Kyoto, Japan), the fluorescence of clarified lysates of GFPUV and rGFPUV, as well as respective enriched fractions, were measured. For all fluorometric measurements, samples were excited at 395 nm and the emission was recorded at 510 nm. A calibration curve was initially prepared by adding different volumes of $GFP_{UV}$ samples to 2 ml of deionized water. The fluorescence of the equal weight of enriched $GFP_{UV}$ and $rGFP_{UV}$ fractions was measured. Following this, equal fluorescence units of $GFP_{UV}$ and $rGFP_{UV}$ fractions were digested with cyanogen bromide at various concentrations. The optimum conditions for a slow cyanogen bromide digestion reaction in the presence of acetic acidic was found to be 100 µl of 12.5 mM CNBr, 1 ml 1.2 M acetic acid and 1 ml of enriched protein fraction by trial and error approach. Using a data acquisition system, the fluorometer readings were collected and recorded every 5 seconds over a period of 6 hours.

Results

The resistant variant of $GFP_{UV}$ ($rGFP_{UV}$) was designed by altering the gene sequence of $GFP_{UV}$. In $GFP_{UV}$ the three methionine residues residue numbers 78, 88, and 218—are well buried in the three dimensional barrel structure. The residue 78 adopts a 3-10 helix, residue 88 is found in a turn and residue 218 is adopts a beta-strand. Based on available structural and bioinformatics information, a cleavage resistant $GFP_{UV}$ was designed in which all methionines were replaced by a neutral residue leucine that neither prefers a helix nor a beta sheet. Additionally, the synthetic gene was designed with two sticky ends for the NCoI and ECoRI restriction sites at the 5' and 3' ends, respectively. For the synthetic construction of resistant variant of $GFP_{UV}$ ($rGFP_{UV}$), the nucleotide sequence used CTG to code for leucine instead of methionine, except for the start codon. CTG was chosen as the leucine coding nucleotide sequence since it constitutes about 50% leucine in E. coli.

Figure 1:
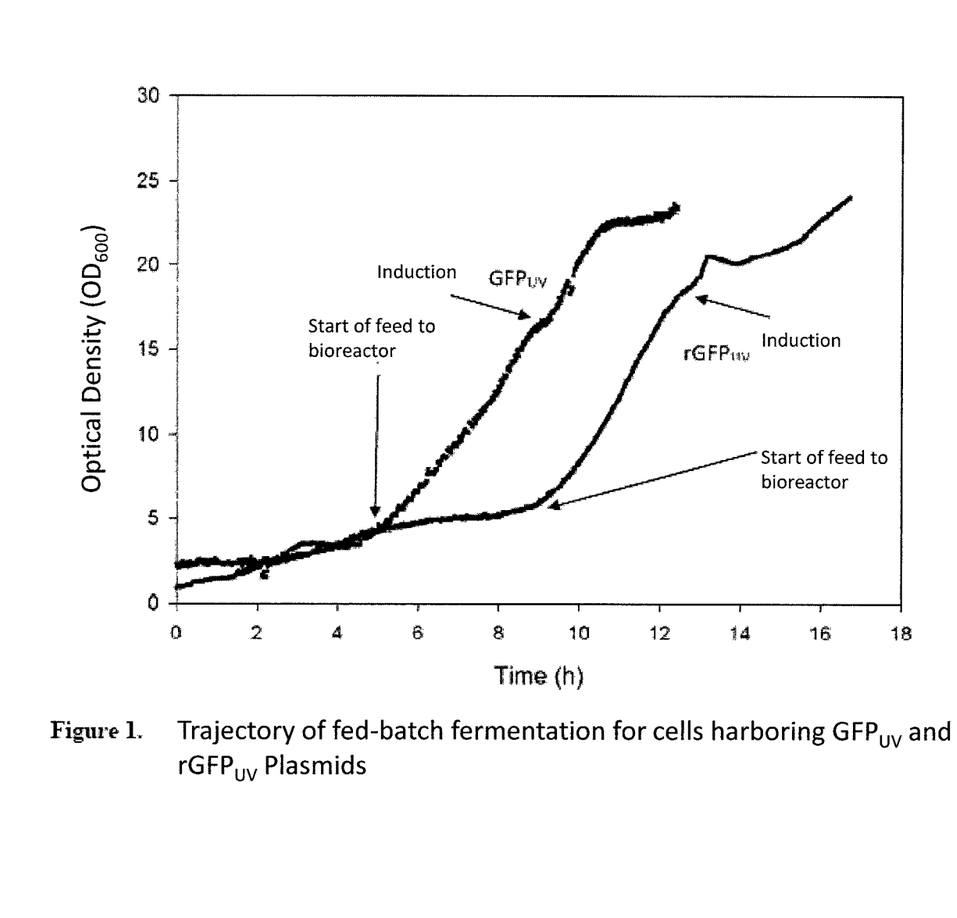
FIG. 1 illustrates a representative growth profile for cells harboring $GFP_{UV}$ and $rGFP_{UV}$ plasmid, respectively.

Cells transformed with $rGFP_{UV}$ plasmid were visibly green under UV light after plating on LBagar plates containing 100 µg/ml ampicillin and 2 mg/ml arabinose. The fed-batch fermentation of cells containing either plasmid followed comparable growth trends and yielded about 60 g/L of cell pellet (wet cell weight/L of media). FIG. 1 shows a representative growth profile for cells harboring $GFP_{UV}$ and $rGFP_{UV}$ plasmid, respectively. Data from repeated runs show that cells harboring either plasmids have similar growth profiles with a specific growth rates of 0.23 h-1 in the exponential phase and reaching final optical density of 23. This demonstrates that the replacement of the four methionine residues of $GFP_{UV}$ by leucine does not affect the growth characteristics as compared to cells harboring $GFP_{UV}$ plasmid.

Figure 2A:
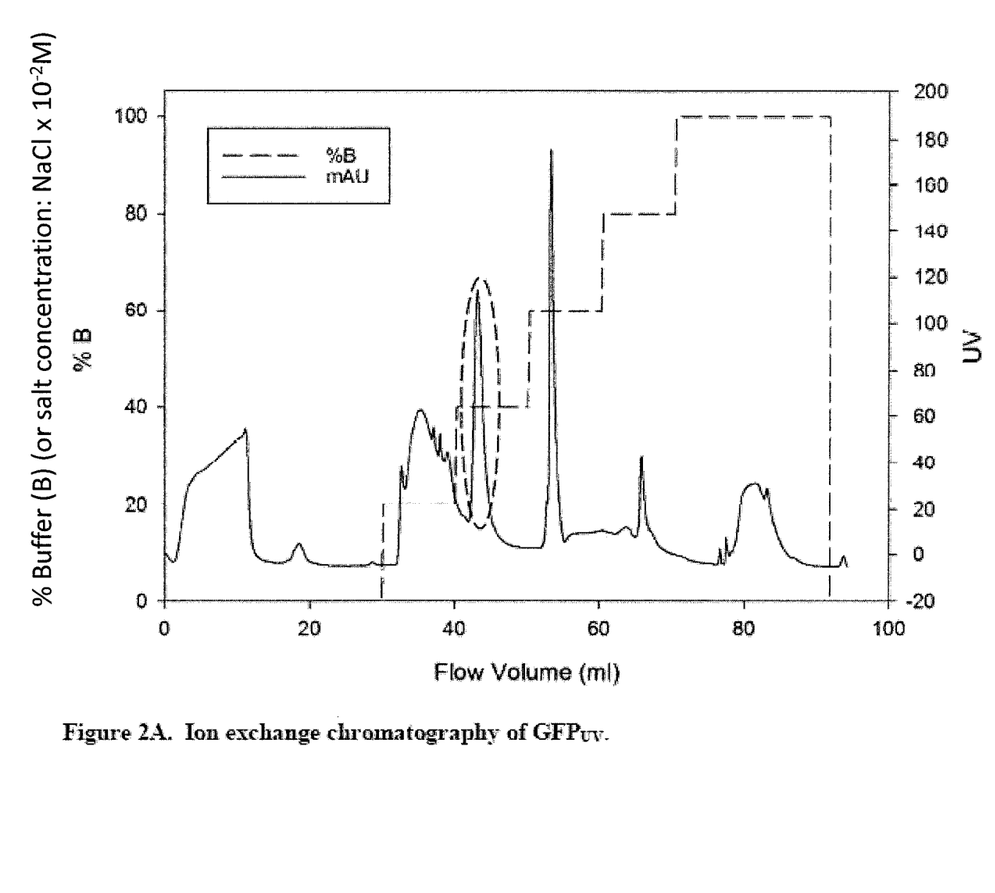
FIG. 2A is an ion exchange chromatogram of $GFP_{UV}$ according to some embodiments.
Figure 2B:
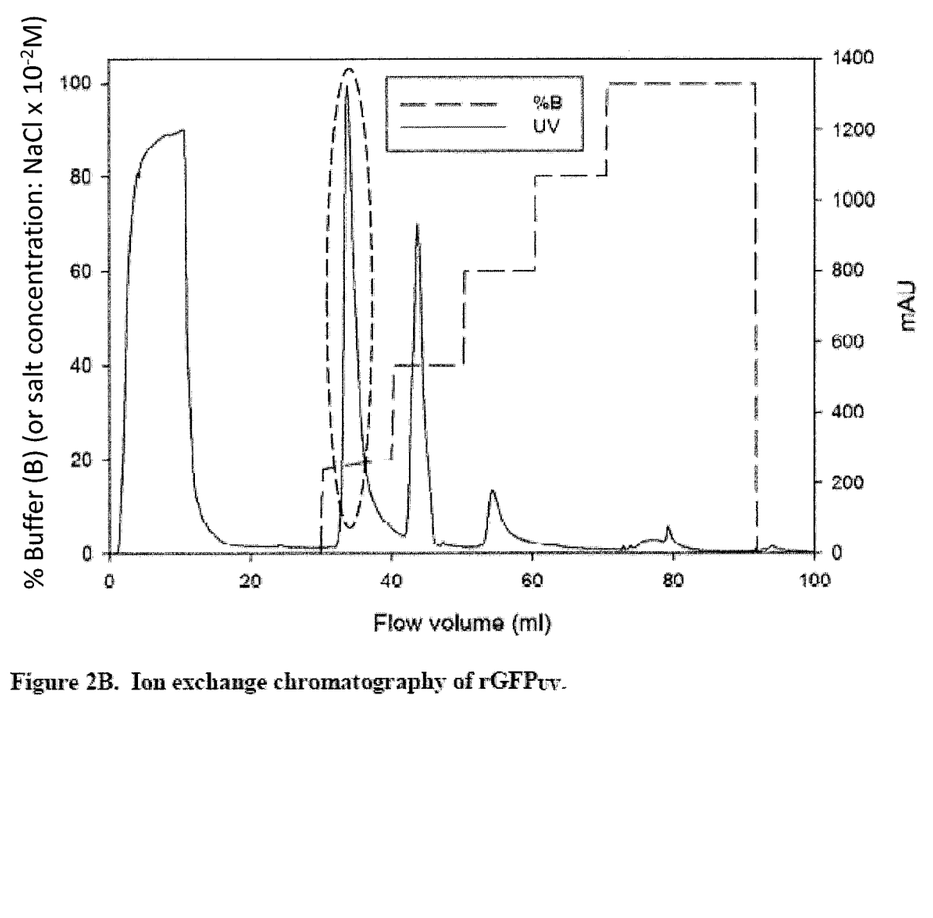
FIG. 2B is an ion exchange chromatogram of $rGFP_{UV}$ according to some embodiments.
Figure 3:
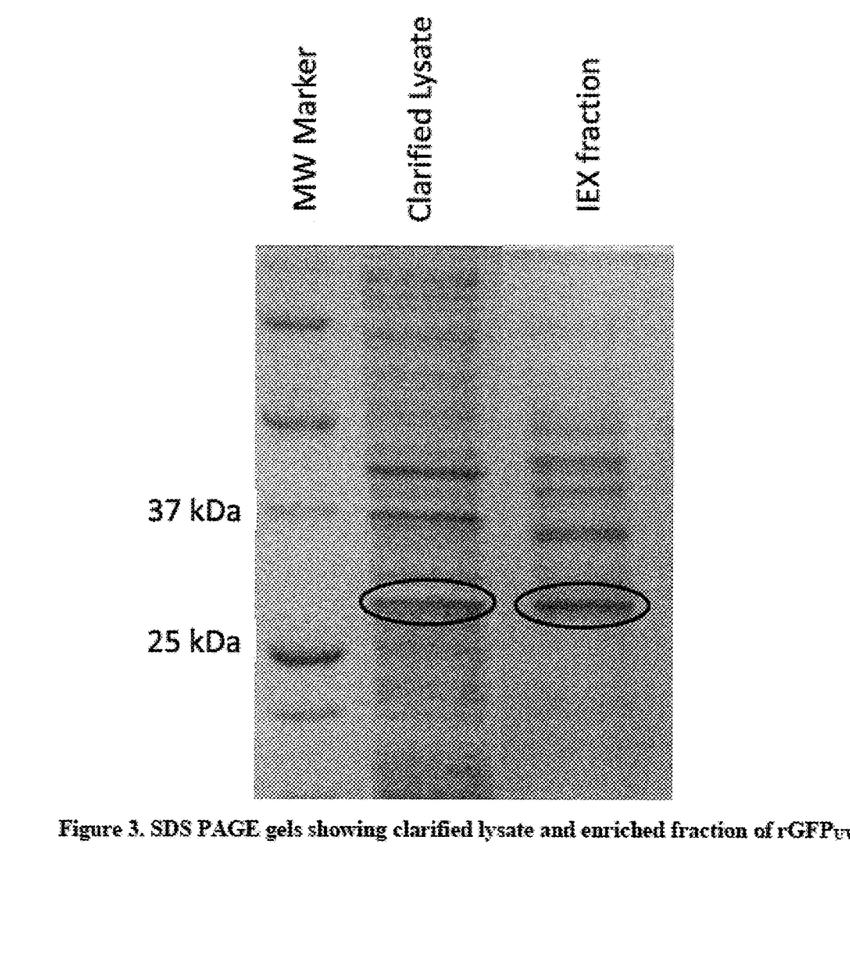
FIG. 3 is an SDSPAGE gel showing the clarified lysate and enriched $rGFP_{UV}$ fraction that was obtained after the one step enrichment process.
Figure 4:
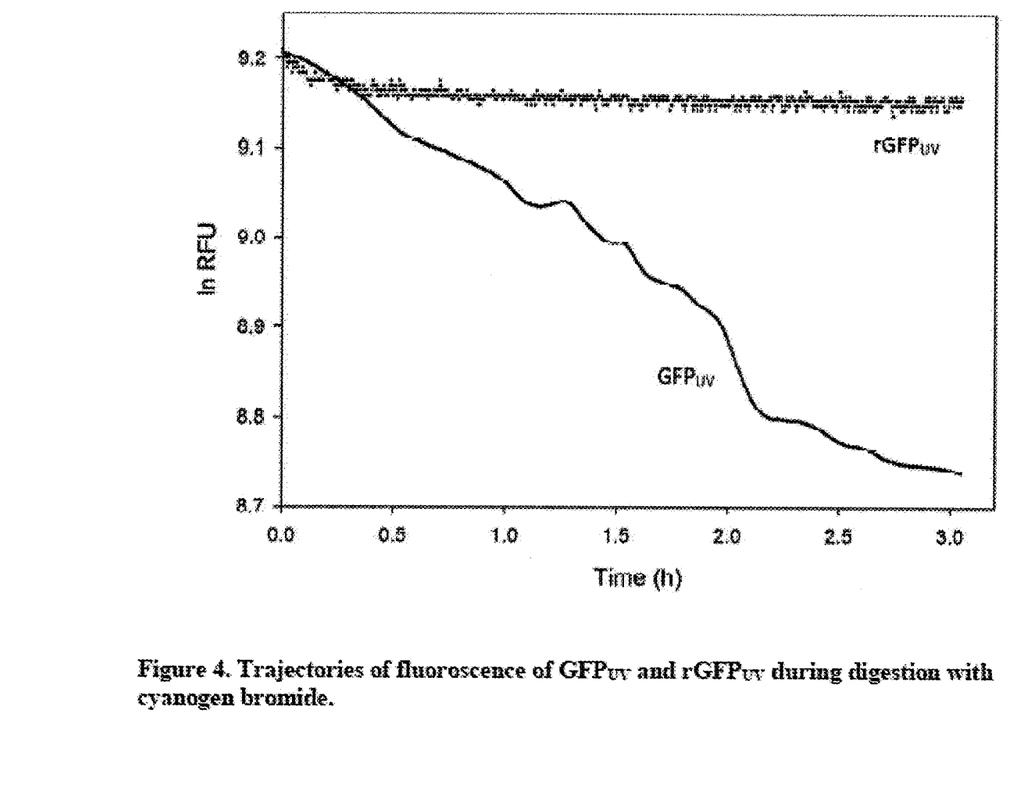
FIG. 4 illustrates the track of natural log of fluorescence signal for both $GFP_{UV}$ and $rGFP_{UV}$ as a function of time when treated with cyanogen bromide under acidic conditions.

Clarified lysates from cell pellets were used to obtain enriched fractions of $GFP_{UV}$ and $rGFP_{UV}$ by fast protein liquid chromatography. A final gradient consisting of five steps (FIGS. 2A and 2B) was used for the single column enrichment process for both $rGFP_{UV}$ and $GFP_{UV}$. In FIG. 2A, the chromatogram tracks the UV signal at 280 nm and % Buffer B (can also be reported as the salt concentration: NaCl×10² M) on the y-axes as a function of flow volume (ml). The $GFP_{UV}$ is eluted as the peak coming off the DEAE resin at 40% B (0.4M NaCl) as indicted by the encircled area. In FIG. 2B, the chromatogram tracks the UV signal at 280 nm and % Buffer B (can also be reported as the salt concentration: NaCl×10² M) on the Y-axes as a function of flow volume (ml). The $rGFP_{UV}$ is eluted as the peak coming off the DEAE resin at 20% B (0.2 M NaCl) as indicated by the encircled peak. FIG. 3 is an SDSPAGE gel showing the clarified lysate and enriched $rGFP_{UV}$ fraction that was obtained after the one step enrichment process. The fluorescence of samples containing equal weight of $rGFP_{UV}$ and $GFP_{UV}$ was found to fluoresce similarly. FIG. 4 shows the track of natural log of fluorescence signal for both $GFP_{UV}$ and $rGFP_{UV}$ as a function of time when treated with cyanogen bromide under acidic conditions. The decay of fluorescence corresponding $GFP_{UV}$ and the lack of it for $rGFP_{UV}$ sample digested using identical cyanogen bromide digestion protocol demonstrates and confirms that under optimal conditions the variant $GFP_{UV}$ is resistant to CNBr induced chemical cleavage. Furthermore, the decay constant for loss of fluorescence was calculated to be 0.17 h-1 from the following relation:

$$\ln RFU(t) = \ln(RFUi) - (\lambda * t)$$

SEQUENCE LISTING FREE TEXT

Cleavage Resistant Photoluminescent Proteins and Applications Thereof

The invention claimed is:

1. A photoluminescent protein comprising:
an amino acid sequence having an absence of internal methionine residues, wherein each internal methionine residue is substituted with an amino acid inert to cyanogen bromide (CNBr), and at least three internal methionine residues are each substituted by a leucine residue.

2. The photoluminescent protein of claim 1, wherein the photoluminescent protein is a green fluorescent protein.

3. The photoluminescent protein of claim 2, wherein the amino acid sequence of the green fluorescent protein includes the sequence of SEQ ID NO:1.

4. The photoluminescent protein of claim 1, wherein the photoluminescent protein is selected from the group consisting of blue fluorescent protein, cyan fluorescent protein, yellow fluorescent protein and red fluorescent protein and wherein the internal methionine residues are substituted with one or more amino acids inert to CNBr.

5. A recombinant protein composition comprising:
a first amino acid sequence of a target protein; and
a photoluminescent protein coupled to the first amino acid sequence, the photoluminescent protein comprising an amino acid sequence having an absence of internal methionine residues, wherein each internal methionine residue is substituted with an amino acid inert to CNBr and at least three of the substituted amino acids is leucine.

6. The recombinant protein composition of claim 5, wherein the photoluminescent protein is a green fluorescent protein.

7. The recombinant protein composition of claim 1, wherein the amino acid sequence of the green fluorescent protein includes the sequence of SEQ ID NO:1.

8. The recombinant protein composition of claim 5, wherein the photoluminescent protein is selected from the group consisting of blue fluorescent protein, cyan fluorescent protein, yellow fluorescent protein and red fluorescent protein and wherein the internal methionine residues are substituted with one or more amino acids inert to CNBr.

9. A method of purifying recombinant protein composition comprising:
providing a mixture including the recombinant protein composition, the recombinant protein composition comprising a first amino acid sequence of a target protein and a photoluminescent protein coupled to the first amino acid sequence, the photoluminescent protein including an amino acid sequence having an absence of internal methionine residues; and
treating the recombinant protein composition with CNBr to release the recombinant protein from an intact photoluminescent protein.

10. The method of claim 9, wherein the photoluminescent protein is a green fluorescent protein and wherein the internal methionine residues are substituted with one or more amino acids inert to CNBr.

11. The method of claim 10, wherein the one or more substitute amino acids is leucine.

12. The method of claim 11, wherein the amino acid sequence of the green fluorescent protein includes the sequence of SEQ ID NO:1.

13. The method of claim 8, wherein the photoluminescent protein is selected from the group consisting of blue fluorescent protein, cyan fluorescent protein, yellow fluorescent protein and red fluorescent protein and wherein the internal methionine residues are substituted with one or more amino acids inert to CNBr.

14. The method of claim 8 further comprising separating the recombinant protein from the intact photoluminescent protein.

15. The method of claim 14, wherein separating comprises loading the recombinant protein and intact photoluminescent protein on a chromatographic column.

16. The photoluminescent protein of claim 1, wherein the photoluminescent protein substantially retains its native photoluminescent intensity.

17. The photoluminescent protein of claim 2, wherein the green fluorescent protein is a $GPF_{UV}$ variant.

18. The photoluminescent protein of claim 1, wherein the photoluminescent protein is substantially free of additional amino acid mutations.

19. A photoluminescent protein comprising:
an amino acid sequence having an absence of internal methionine residues, wherein internal methionine residues are substituted with amino acids inert to cyanogen bromide (CNBr), and the photoluminescent protein retains photoluminescent intensity of an unsubstituted photoluminescent protein comprising the internal methionine residues.

* * * * *

```
                            SEQUENCE LISTING

<160> NUMBER OF SEQ ID NOS: 1

<210> SEQ ID NO 1
<211> LENGTH: 240
<212> TYPE: PRT
<213> ORGANISM: Artificial Sequence
<220> FEATURE:
<223> OTHER INFORMATION: Cyanogen Bromide Cleavage Resistant Green
      Fluorescent Protein

<400> SEQUENCE: 1

Met Gly Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Ser Tyr Gly Val Gln Cys Phe Ser Arg Tyr Pro Asp His Leu Lys
65                  70                  75                  80

Arg His Asp Phe Phe Lys Ser Ala Leu Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Leu Val Leu Leu Glu Phe
    210                 215                 220

Val Thr Ala Ala Gly Ile Thr His Gly Leu Asp Glu Leu Tyr Lys Glu
225                 230                 235                 240
```